United States Patent [19]
Rieke

[11] Patent Number: 5,852,200
[45] Date of Patent: Dec. 22, 1998

[54] CROSS-COUPLING OF ORGANIC COMPOUNDS USING CUPROUS IODIDE

[75] Inventor: Reuben D. Rieke, Lincoln, Nebr.

[73] Assignee: Rieke Metals, Inc., Lincoln, Nebr.

[21] Appl. No.: 701,628

[22] Filed: Aug. 22, 1996

Related U.S. Application Data

[60] Provisional application No. 60/009,330, Dec. 28, 1995.
[51] Int. Cl.$^6$ .................................................... C07C 69/76
[52] U.S. Cl. .............................. 560/51; 560/54; 560/126; 560/174; 560/205; 568/309; 568/319; 568/346; 568/348; 568/397; 568/398; 568/412
[58] Field of Search ............................... 560/51, 54, 126, 560/174, 205; 568/309, 319, 346, 348, 397, 398, 412

[56] References Cited

U.S. PATENT DOCUMENTS 5,358,546  10/1994  Rieke ........................................ 75/252

OTHER PUBLICATIONS

Journal of The American Chemical Society, vol. 106, No. 11, 30 May 1984, DC US, pp. 3368–3370, XP002030288 E. Nakamura: "Copper-Catalyzed Acylation and Conjugate Addition of Zinc Homoenolate. Synthesis of 4- and 6-oxo esters."

Tetrahedron Letters, vol. 35, No. 39, 26 Sep. 1994, Oxford GB, pp. 7205–7208, XP00465075, M.V. Hanson, "Direct Formation of Secondary and Tertiary Alkylzinc Bromides".

J. Org. Chem. 1988, 53, 2390–2392.

The Direct Formation of Functionalized Alkyl (aryl) zinc Halides by Oxidative Addition of Highly Reactive Zinc with Organic Halides and Their Reactions with Acid Chlorides, $\alpha,\beta$–Unsaturated Ketones, and Allylic, Aryl, and Vinyl Halides, The Journal of Organic Chemistry, 1991, vol. 56, pp. 1445–1453.

1,4–Additions of the Highly Functionalized Copper Reagents RCu(CN)Znl . 2 BF$_3$ to Trisubstituted Enones. A New BF$_3$ Promoted Cyclization Reaction, Tetrahedron Letters, Yeh et al., vol. 29, No. 51, pp. 6693–6696, 1988.

2–Cyanoethylzinc Iodide: A New Reagent with Reactivity Umpolung, Tetrahedron Letters, Yeh and Knochel, vol. 29, No. 20, pp. 2395–2396, 1988.

Zhu et al., Tetrahedron Lett., vol. 32, p. 2865 (1991).

B.M. Trost and R. A. Kunz, J. Org. Chem. 39, 2648 (1974).

*Primary Examiner*—Paul J. Killos
*Attorney, Agent, or Firm*—Merchant, Gould, Smith, Edell, Welter & Schmidt, P.A.

[57] ABSTRACT

Cross-coupling or addition reactions of organic compounds, including acid halides, allylic halides, and $\alpha,\beta$-unsaturated carbonyl containing compounds, with organozinc compounds may be readily and safely carried out in the presence of cuprous iodide. The use of this catalyst in the coupling reaction provides for the preparation of commercially useful products in the pharmaceutical, agrochemical and other industries.

6 Claims, No Drawings

CROSS-COUPLING OF ORGANIC COMPOUNDS USING CUPROUS IODIDE

This is a continuation of U.S. patent application Ser. No. 60/009,330, filed Dec. 28, 1995.

FIELD OF THE INVENTION

This invention is directed to the use of cuprous iodide to catalyze the reaction of organozinc compounds with various organic compounds, including acid halides, allylic halides, and α, β-unsaturated carbonyls.

BACKGROUND OF THE INVENTION

The coupling reactions of organozinc reagents with reactive organic compounds, including carboxylic acid halides, allylic halides, and α, β-unsaturated carbonyl compounds, are generally known in the art. See, for example, Knochel et al., *J. Org. Chem.* Vol. 53, p. 2392 (1988); Wehmeyer et al., *J. Org. Chem.* Vol. 56, p. 1445 (1991); and Zhu et al., *Tetrahedron Lett.* Vol. 32, p.2865 (1991). Such reactions find wide use in organic synthesis, such as in the preparation of pharmaceuticals, agrochemicals and other products. However, these reactions have so far only been effectively catalyzed by the complexes of cuprous cyanides CuCN.2LiBr, CuCN.LiBr, and CuCN.LiCl. Use of a cyanide containing reagent like CuCN creates a number of problems during reaction and workup procedures, including safety and disposal concerns.

There is a clear need for a method of catalyzing these cross-coupling reactions that makes use of a catalyst that is readily available and does not present the problems associated with the use of cuprous cyanide or other cyanide containing reagents.

SUMMARY OF THE INVENTION

It has now been found that reactions between organozinc compounds and organic compounds such as acid halides, allylic halides, and α, β-unsaturated carbonyl containing compounds are effectively carried out in the presence of cuprous iodide (CuI).

Accordingly, the invention provides a method of coupling a carboxylic acid halide and an organozinc compound, the method comprising reacting the carboxylic acid halide with the organozinc compound in the presence of cuprous iodide (CuI).

The invention also provides a method of coupling an allylic halide and an organozinc compound, the method comprising reacting the allylic halide with the organozinc compound in the presence of cuprous iodide.

The invention further provides a method of adding an organozinc compound to an α,β-unsaturated carbonyl containing compound, the method comprising reacting the organozinc compound with the α,β-unsaturated carbonyl containing compound in the presence of cuprous iodide.

As used herein the terms "alkyl" and "alkylene" are inclusive of acyclic and cyclic straight and branched chain alkyl and alkylene groups.

The term "aryl" as used herein is inclusive of single and polycyclic hydrocarbyl aromatic and heteroaromatic groups. Examples of aryl groups include benzene, naphthalene, pyridine, thiophene, furan, and the like.

The term "α,β-unsaturated carbonyl containing compound" is inclusive of α,β-unsaturated ketones as well as other compounds containing α,β-unsaturated carbonyl functionality. Examples of such compounds include α,β-unsaturated aldehydes, amides, esters, and the like.

The term "substituted" as applied to any substituent group includes those groups that are substituted by a non-hydrogen substituent group. Such groups include, for example, hydrogen, hydroxy, alkyl, alkenyl, alkoxy, aryl, aralkyl, aralkenyl, ether, amino, alkylamino, dialkylamino, carboxylic acyl, carboxylic acid ester, carbamoyl, carbamate, nitrile, oxo, and ketone groups.

DETAILED DESCRIPTION OF THE INVENTION

As set forth above, the invention provides methods of coupling various organic compounds, including acid halides, allylic halides, and α, β-unsaturated carbonyl containing compounds, with organozinc compounds by using CuI as a catalyst. Various aspects of the invention are now discussed in greater detail.

The Organozinc Compound

Any desired organozinc compound may be used in the method of the invention, including functionalized and/or substituted organozinc compounds. Examples of such organozinc compounds include organozinc compounds of formula (1):

$$R-Zn-X \qquad (1)$$

wherein X is a halogen atom and R is selected from the group consisting of alkyl, substituted alkyl, alkenyl, substituted alkenyl, aryl, aralkyl, aralkenyl and substituted aryl, aralkyl, and aralkenyl.

Preferred organozinc compounds include those wherein X is I, Cl or Br, and R is a substituted alkyl, substituted alkenyl, substituted aryl, substituted aralkyl, or substituted aralkenyl group.

The organozinc compounds useful in the method of the invention may be prepared by methods known to those of skill in the art, including those described by Rieke in U.S. Pat. No. 5,358,546, the disclosure of which is incorporated herein by reference.

The Cuprous Iodide Catalyst

Cuprous iodide is a well known and readily available catalyst. The CuI may be used alone or in combination with another reagent if desired, for example to increase the solubility of the CuI in the chosen solvent. For example, CuI alone is insoluble in THF, but if a molar proportion of a lithium halide such as LiBr, LiCl or LiI equal to the molar proportion of CuI present is added, a majority of the CuI dissolves in the THF. While the invention is not bound by any theory of operation, it is believed that a complex of CuI and the lithium halide is formed and that this complex can also function to catalyze cross-coupling and addition reactions between organozinc compounds and organic compounds.

An effective amount of the CuI catalyst is present in the reaction mixture to allow the cross-coupling or addition reaction to proceed to completion. Typically, this is about 0.0001 to 1.0 moles of CuI per mole of organozinc compound used, with about 0.05 to 0.10 moles CuI per mole of organozinc compound preferred.

Cross-Coupling Reaction with Acid Halides

Generally, the cross-coupling of an organozinc compound with an acid halide catalyzed with CuI according to the method of the invention follows reaction scheme (I):

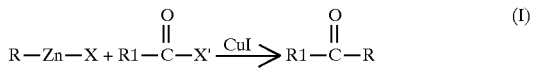

wherein R and X are as described supra, X' is a halogen atom and R1 represents a non-aldehyde containing organic radical. Preferably, X is I, Br or Cl and R1 is selected from the group consisting of alkyl, substituted alkyl, alkenyl, substituted alkenyl, amino, substituted amino, aryl, aralkyl, aralkenyl, substituted aryl, substituted aralkyl, and substituted aralkenyl. More preferably, X is Br; X' is Cl or Br; and R and R1 are independently selected from the group consisting of substituted alkyl, substituted alkenyl, substituted aryl, substituted aralkyl, and substituted aralkenyl.

The CuI catalyzed coupling reaction between the organozinc compound and the acid halide is preferably carried out in an organic solvent. Any organic solvent which will not interfere with the reaction may be used. Suitable types of organic solvents include, for example, alcohols, hydrocarbons having about 4 to 80 carbon atoms, ethers, ketones, and the like. Preferred solvents include dimethoxyethane, dioxane, diethoxymethane, ethylene glycol dibutyl ether, and THF, with THF especially preferred.

To carry out the reaction, the CuI and if desired the lithium halide is placed into a suitable reaction vessel along with the organozinc compound and solvent. The reaction is preferably carried out under an inert atmosphere, such as argon or nitrogen. The mixture is stirred until uniform and cooled to a temperature of about −100° C. to room temperature (about 25° C.), preferably to about −40° C. to −20° C.

When the mixture reaches the desired temperature, the acid halide is added. The addition may be accomplished in any known manner. Generally, the molar ratio of organozinc compound to acid halide is about 2:1 to 1:3, with 1:0.8 preferred. The reaction mixture is stirred typically for about 5 to 300 minutes, preferably about 20 to 30 minutes. At this point the reaction is complete and the product may be allowed to warm to room temperature if desired. The product may be used as is or isolated.

One particular type of reaction of an organozinc compound with an acid halide provides a new synthetic route to the preparation of functionalized benzil molecules. Using the method of the invention, aryl or substituted aryl organozinc compounds can be reacted with oxalyl chloride or oxalyl bromide in the presence of CuI. Such reactions generally follow reaction scheme (Ia):

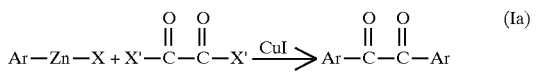

wherein Ar is an unsubstituted or substituted aryl group and X' is a halogen atom. Preferably Ar is an unsubstituted or substituted benzene group, and most preferably Ar is a substituted benzene group. X' is preferably Cl or Br.

To prepare the benzil molecule, the CuI and lithium halide, if a lithium halide is used, is placed in a reaction vessel under an inert atmosphere. The organic solvent is added with stirring and the temperature of the mixture adjusted to about −100° C. to room temperature (about 25° C.), preferably to about −40° C. to −20° C. The organozinc compound is then added and stirring continued. The oxalyl halide is added and if at a reduced temperature the reaction mixture allowed to come to room temperature while stirring continues. The product may be isolated or used directly.

Cross-Coupling Reaction with Allyl Halides

The CuI catalyzed cross-coupling reaction of an organozinc compound and an allyl halide follows one of the general reaction schemes (IIa–IIc):

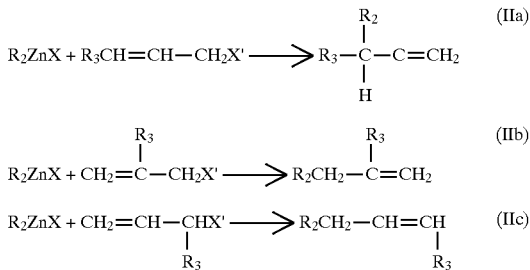

wherein X and X' are each halogen; R2 is selected from the group consisting of H, alkyl, substituted alkyl, alkenyl, substituted alkenyl, aryl, aralkyl, aralkenyl, substituted aryl, substituted aralkyl, and substituted aralkenyl; and R3 is selected from the group consisting of alkyl substituted alkyl, alkenyl, substituted alkenyl, aryl, aralkyl, aralkenyl substituted aryl, substituted aralkyl and substituted aralkenyl. In a preferred embodiment, R2 and R3 are independently selected from the group consisting of substituted alkyl, substituted alkenyl, substituted aryl, substituted aralkyl, and substituted aralkenyl.

To carry out the reaction, the CuI and lithium halide, if used, are placed into a suitable reaction vessel along with the organozinc compound and solvent. The solvent is preferably in organic solvent as described supra. This reaction is preferably carried out under an inert atmosphere, such as argon or nitrogen. The mixture is stirred until uniform and the temperature adjusted to about −100° C. to room temperature (about 25° C.), preferably about −40° C. to −20° C.

When the mixture is at the desired temperature, the allyl halide is added. The addition may be accomplished in any known manner. Generally, the molar ratio of organozinc compound to allylic halide ranges from about 3:1 to 1:3, with a 1:1 ratio preferred. This reaction mixture is stirred for about 5 to 300 minutes, preferably about 20 to 30 minutes. If cooled, the reaction mixture may be maintained at the reduced temperature or allowed to rise freely to room temperature. When the reaction is complete the product is worked up using a method known in the art. Yields for this reaction are typically about 90 to 98%.

Addition to α,β-Unsaturated Carbonyl Containing Compounds

The CuI catalyzed addition of organozinc compounds to enones according to the invention proceeds according to reaction scheme (III):

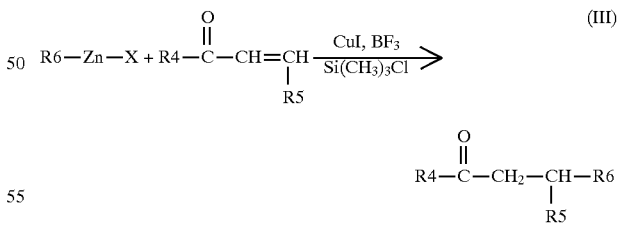

wherein X is as defined above; R4 and R5 are independently selected from the group consisting of H, alkyl, substituted alkyl, alkenyl, substituted alkenyl, amino, substituted amino, alkoxy, substituted alkoxy, aryl, aralkyl, aralkenyl substituted aryl, substituted aralkyl, and substituted aralkenyl, or R4 and R5 together form a —$(CH_2)_n$— group, wherein n is 2 to 4; and R6 is selected from the group consisting of alkyl, substituted alkyl, alkenyl, substituted alkenyl, aryl, substituted aryl, amino, substituted amino, alkoxy, substituted alkoxy, aralkyl, substituted aralkyl, aralkenyl, and substituted aralkenyl. In a preferred embodiment R4, R5 and R6 are independently selected from the group consisting of substituted alkyl, substituted alkenyl, substituted amino, substituted alkoxy, substituted aryl, substituted aralkyl, and substituted aralkenyl.

CuI and lithium halide, if used, along with the desired solvent are placed in a reaction vessel. The organozinc reagent is then added to the vessel. The reaction is preferably carried out under an inert atmosphere, such as argon or nitrogen. The mixture is stirred until uniform and the temperature adjusted to about −100° C. to room temperature (about 25° C.), preferably about −40° C. to −20° C.

When the mixture is cooled, the enone compound is added to the reaction vessel. To improve the yield of this reaction, $BF_3$ and $Si(CH_3)_3Cl$ are also present. They are generally added to the reaction vessel at the same time as the enone compound. Generally, the molar ratio of organozinc compound to enone ranges from about 1:1 to 3:0.5, with 1:0.7 preferred. For any given proportion of organozinc compound to enone, $BF_3$ is present in an amount of about 0.1 to 5.0 moles, preferably about 1.5 moles, and $Si(CH_3)_3Cl$ is present in an amount ranging from about 0.1 moles to 5.0 moles, preferably about 2.0 moles.

The reaction mixture is stirred for about 5 to 300 minutes, preferably about 20 to 30 minutes. During this time the reaction mixture, if cooled, may be maintained at a reduced temperature or allowed to rise to room temperature. When the reaction is complete the product may be used as is or worked up in a manner known in the art.

The invention is further described by reference to the following examples, which are understood to be illustrative and not limiting of the invention.

EXAMPLE 1

Preparation of 7-Chloro-1-phenyl-1-heptanone

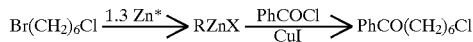

Preparation of Organozinc: A 500 mL round bottomed flask was placed under Argon and 17 grams (0.25 mol) of zinc was added in 240 mL THF at rt. An ice bath was placed around the flask and 1-bromo-6chlorohexane 39.0 grams (0.2 mol) was added slowly via syringe and stirred 1 h at 0° C. and a quench was taken. 90% was converted to 1-chlorohexane via GC analysis. After removing the ice bath the rxn was allowed to warm to room temperature and stir 2 more h. The stirring was ceased and the reaction was allowed to stand overnight.

Coupling of RZnX: CuI 3.6 grams (0.19 mol) was placed into a 500 mL round bottomed flask in the air and placed under an atmosphere of Argon 10 mL THF was added at room temperature and stirred for 10 min at that temperature. The flask was cooled to −40° C. and benzoyl chloride 21.0 grams (0.15 mol) was added. After stirring for 4 h the reaction temperature had reached room temperature and GC showed a clean reaction had occurred. After workup and distillation [2 mm Hg; 155°–158° C.] 19.6 grams of product were obtained for an isolated yield of 65%.

EXAMPLE 2

Preparation of 1-(4-Bromophenyl)-7-chloro-1-oxoheptane

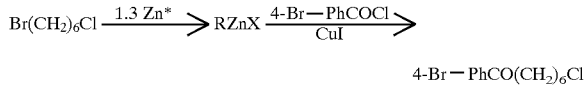

Preparation of RZnX: This organozinc was not freshly prepared but was prepared in 4/93 and 11/94. Coupling of RZnX: The same procedure as before was followed except 4-Bromobenzoyl chloride, 35.0 grams (0.16 mol) dissolved in 10 mL THF was used. After stirring 3 h from −40° C. to room temperature the reaction product was worked up by adding hot hexanes to the resulting solid until it went into solution, cooled to room temperature slowly and placed into the freezer. A very pure looking white solid was obtained. The hexanes were drained off, providing a yield of 75% of product having a melting point of 44°–46° C.

EXAMPLE 3

Reaction of an Aryl Organozinc with Oxalyl Chloride Mediated by CuI

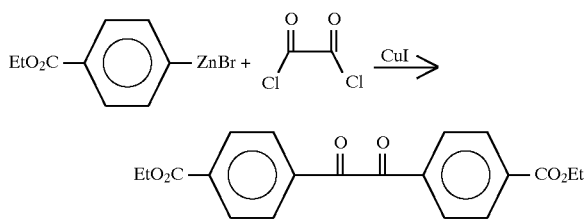

Preparation of Organozinc: As previously described.

Cross-coupling of Organozinc with Oxalyl Chloride: CuI 0.11 grams (0.6 mmol) was placed into a 50 mL round bottomed flask and put under an atmosphere of argon. 3 mL THF was added and stirred 5 min, cooled to −40° C. and the organozinc was added (10 mL of 0.6M in THF). This was stirred 15 min at that temperature, and the oxalyl chloride 0.3 grams (2.4 mmol) was added. This reaction was completed in 1 h with a 60 to 80% yield.

EXAMPLE 4

Cross-coupling Reaction of Organozinc Compound with Allyl Bromide

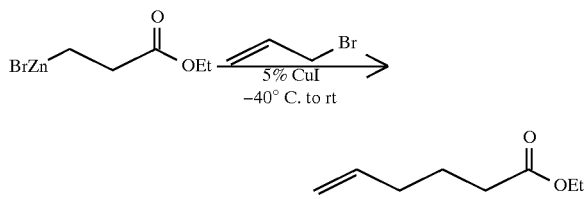

Preparation of organozinc compound: Prepared as previously reported.

Coupling of RZnX: CuI 0.11 grams (0.6 mmol) was placed into a 50 mL round bottomed flask and placed under an atmosphere of Argon. 3 mL THF was added at room temperature and stirred for 10 min. The organozinc compound (6 mmol) in THF was then added to the flask via a disposable syringe. The flask was cooled to −40° C. and allyl bromide 0.6 grams (5 mmol) was added. After stirring for 2 h the reaction temperature had reached room temperature and GC showed a clean reaction and conversion to product had occurred.

EXAMPLE 5

CuI Mediated Conjugate Addition of Organozinc Compound with an α,β-Unsaturated Ketone

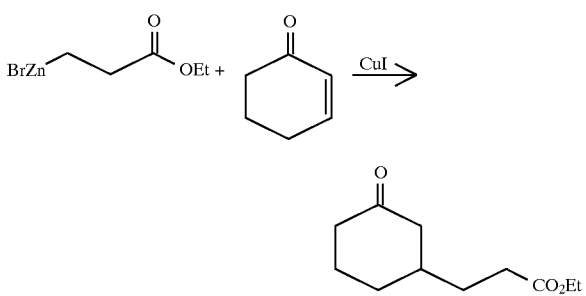

Preparation of organozinc compound: As previously described.

Conjugate Addition of Organozinc: CuI 0.11 grams (0.6 mmol) was placed into a 50 mL round bottomed flask and put under an atmosphere of argon. 3 mL THF was added and stirred 5 min and cooled to −40° C., and then the organozinc was added (10 mL of 0.6M in THF). This was stirred 15 min at −40° C. and TMS-Cl (1.3 grams, 12 mmol), $BF_3$-$OEt_2$ (1.2 grams, 9 mmol) and the enone (0.46 grams, 4.8 mmol) were added. This was allowed to warm to room temperature over 4 h. The reaction is very clean and provides a yield of about 70 to 90%.

EXAMPLE 6

Synthesis of Methyl 3-Oxo-4-pentenoate

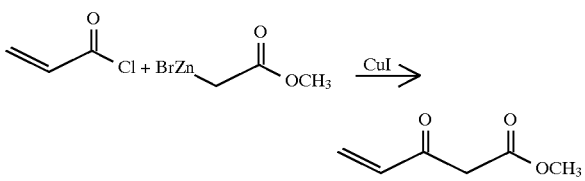

The utility of methyl-e-oxo-4-pentenoate as an annelating agent in the synthesis of terpenes and alkaloids has been previously demonstrated by B. M. Trost and R. A. Kunz, *J. Org. Chem.*, 39, 2648 (1974) and references therein. In the aforementioned reference, Trost reports the synthesis of this molecule in 60–76% isolated yield.

Preparation of Organozinc: Into a 100 mL round bottomed flask was placed ZN* (2 grams, 0.030 mol in 40 mL THF) under an atmosphere of argon. Methyl bromoacetate (4.13 grams, 0.027 mol) was added slowly to the Zn* and stirred 2 h at room temperature. After allowing the excess Zn* to settle overnight, the organozinc in THF was ready to react. It should be noted that we have prepared organozinc reagents similar to this one containing alkyl groups other than methyl present in the ester.

Cross-Coupling with Acid Chloride: Into a 100 mL round bottomed flask under an atmosphere of argon was placed CuI (0.51 grams, 0.0027 mol) and 3 mL THF. This was stirred 5 min and cooled to −40° C. and the organozinc (0.27 mol) was added and stirred 15 min at that temperature. Acryloyl chloride (1.90 grams, 0.021 mol) was added via syringe at −40° C. and the reaction was allowed to stir and warm to room temperature over a period of 4 h. After workup and purification methyl 3-oxo-4-pentenoate was afforded in 80–95% yield.

I claim:

1. A process for coupling a carboxylic acid halide, an allylic halide or an α,β-unsaturated carbonyl containing compound with an organozinc compound, consisting of reacting under an inert atmosphere said acid halide, allylic halide or α,β-unsaturated carbonyl containing compound with said organozinc compound at between about −100° C. to about 25° C. in the presence of an organic solvent and in the presence of cuprous iodide as a catalyst.

2. The process of claim 1 wherein cuprous iodide is present in an amount from about 0.05 to about 0.1 mole per mole of organozinc compound.

3. A process of preparing a compound of the formula

wherein R is selected from the group consisting of alkyl, substituted alkyl, alkenyl, substituted alkenyl, aryl, substituted aryl, amino, aralkyl, substituted aralkyl, aralkenyl and substituted aralkenyl, substituted amino, and R1 is alkyl, substituted alkyl, alkenyl, substituted alkenyl, aryl, aralkyl, aralkenyl, substituted aryl, substituted aralkyl or substituted aralkenyl, the process consisting of reacting a compound of the formula

wherein X' is a halogen atom with a compound of the formula

X—Zn—R1 wherein X is I, Br or Cl, and R1 is alkyl, substituted alkyl, alkenyl, substituted alkenyl, aryl, aralkyl, aralkenyl, substituted aryl, substituted aralkyl or substituted aralkenyl under an inert atmosphere between about −100° C. to about 25° C. in the presence of an organic solvent and in the presence of cuprous iodide as a catalyst.

4. The process of claim 2 wherein cuprous iodide is present in an amount from about 0.05 to about 0.1 mole per mole of organozinc compound.

5. A process of preparing a compound of the formula

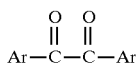

wherein Ar is an unsubstituted or substituted aryl groups, the method consisting of reacting a compound of the formula

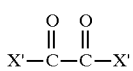

wherein X' is a halogen atom with a compound of the formula

X—Zn—Ar wherein X is a halogen atom, under an inert atmosphere between about −100° C. to about 25° C. in the presence of an organic solvent and in the presence of cuprous iodide as a catalyst.

6. The process of claim 5, wherein cuprous iodide is present in an amount of about 0.05 to about 0.1 mole per mole of organozinc compound.

* * * * *